United States Patent [19]

Stemp et al.

[11] Patent Number: 5,637,609

[45] Date of Patent: Jun. 10, 1997

[54] 2-PHENYLPYRROLE DERIVATIVES AS DOPAMINE $D_3$ RECEPTOR ANTAGONISTS

[75] Inventors: Geoffrey Stemp, Hertfordshire; Christopher N. Johnson, Essex, both of England

[73] Assignee: SmithKline Beecham plc, United Kingdom

[21] Appl. No.: 586,758

[22] PCT Filed: Jul. 21, 1994

[86] PCT No.: PCT/EP94/02412

§ 371 Date: Jan. 29, 1996

§ 102(e) Date: Jan. 29, 1996

[87] PCT Pub. No.: WO95/04039

PCT Pub. Date: Feb. 9, 1995

[30] Foreign Application Priority Data

Jul. 30, 1993 [GB] United Kingdom ............ 9315801

[51] Int. Cl.⁶ .................. A61K 31/40; C07D 207/323
[52] U.S. Cl. ................ 514/422; 514/427; 548/517; 548/525
[58] Field of Search ................... 548/517, 525; 514/422, 427

[56] References Cited

U.S. PATENT DOCUMENTS 5,523,299 6/1996 Stemp et al. .................... 514/183

FOREIGN PATENT DOCUMENTS 0241053 10/1987 European Pat. Off. .
0259930 3/1988 European Pat. Off. .
9403426 2/1994 WIPO .

OTHER PUBLICATIONS

CA 122: 81113b 5-(2-alkoxyphenyl)pyrroles . . . agents. Stemp et al., p. 1065.

J. Med. Chem., vol. 30, 1987, pp. 2099–2104, Van Wijngaarden et al '2-Phenylpyrroles as conformationally restricted benzamide analogues'.

J. Med. Chem., vol. 31, 1988, pp. 1934–1940, Van Wijngaarden et al '2-Phenylpyrroles as conformationally restricted benzamide analogues'.

J. Med. Chem., vol. 35, pp. 2355–2363, I. Pettersson et al 'Conformational Analysis of dopamine D-2 receptor antagonists of the benzamide series in relation to a recently proposed D-2 receptor interaction model'.

*Primary Examiner*—Joseph K. McKane
*Attorney, Agent, or Firm*—Nora Stein-Fernandez; William T. King; Edward T. Lentz

[57] ABSTRACT

A compound of formula (I):

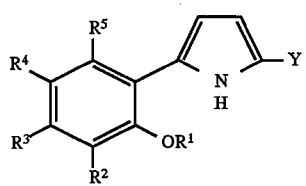

Formula (I)

which have high affinity for dopamine $D_3$ receptors and thus have potential as antipsychotic agents.

11 Claims, No Drawings

2-PHENYLPYRROLE DERIVATIVES AS DOPAMINE $D_3$ RECEPTOR ANTAGONISTS

This application is a 371 of PCT/EP94/02412 filed on Jul. 30, 1994, published as WO95/04039 Feb. 9, 1995.

The present invention relates to novel phenylpyrrole derivatives, processes for their preparation, pharmaceutical compositions containing them and their use in therapy, in particular as antipsychotic agents.

European Patent Application No. 241053, describes compounds of the formula:

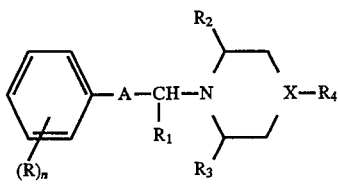

wherein A is an unsaturated 5-membered heterocyclic ring, such as 2,5-pyrrolyl, or 3,5- or 1,4- pyrazolyl; X is a nitrogen or carbon atom; $R_1, R_2, R_3$ are each hydrogen or alkyl; $R_4$ is aryl, heteroaryl, arylcarbonyl or heteroaryl-carbonyl; R is selected from a variety of substituents and n is 0–4. The compounds are said to have antipsychotic properties.

European Patent Application No. 259930 describes compounds of the formula:

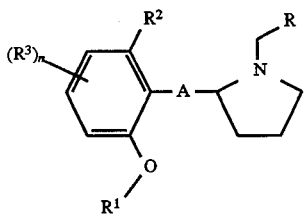

wherein A is an unsaturated 5-membered heterocyclic ring, such as 2,5-pyrrolyl, 1,4-pyrazolyl or 2,5-furyl; R is hydrogen, alkyl or optionally substituted phenyl; $R^1$ is alkyl, alkenyl or forms a ring with the phenyl group; $R^2$ is hydrogen, hydroxy or alkoxy; $R^3$ is selected from a variety of substituents and n is 0–3. These compounds are also said to have antipsychotic properties.

We have now found a novel class of 2-phenylpyrroles which have high affinity for dopamine $D_3$ receptors and thus have potential as antipsychotic agents.

In a first aspect the present invention provides compounds of formula (I):

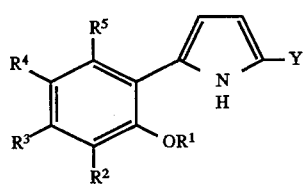

Formula (I)

wherein $R^1$ represents $C_{1-4}$alkyl; and $R^2, R^3, R^4$ and $R^5$ each independently represent hydrogen, halogen, $C_{1-4}$alkyl, $C_{1-4}$alkoxy, $C_{1-4}$alkoxy$C_{1-4}$alkyl, $C_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxy, hydroxyalkyl, $C_{1-4}$alkylthio, $C_{1-4}$alkanoyl, $C_{1-4}$alkoxycarbonyl, $C_{1-4}$alkanoyl, $C_{1-4}$alkoxycarbonyl, $C_{1-4}$alkanoyl, $C_{1-4}$alkoxycarbonyl, or $-SO_2NR^{11}R^{12}$ wherein $R^{11}$ and $R^{12}$ each independently represent hydrogen, $C_{1-4}$alkyl or $C_{1-4}$alkoxy$C_{1-4}$alkyl, or $NR^{11}R^{12}$ forms a 3- to 8- membered fully saturated heterocyclic ring, a 5- to 8-membered partially saturated heterocyclic ring, or a 5- to 8-membered fully saturated heterocyclic ring which contains in addition to the nitrogen atom an oxygen or sulphur atom; or $R^1$ and $R^2$ together form a linking chain $-(CH_2)_mO_p$;

(wherein m is 2 to 4 and p is zero or 1) which chain may be optionally substituted by one or two $C_{1-4}$alkyl groups; and Y represents a group of formula:

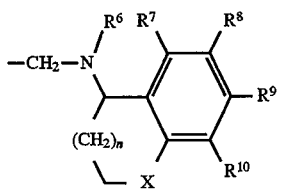

wherein $R^6$ represents $C_{1-6}$alkyl, $C_{3-6}$alkenyl or $C_{3-6}$cycloalkyl$C_{1-4}$alkyl;

$R^7$, $R^8$, $R^9$ and $R^{10}$ each independently represent hydrogen, halogen, $C_{1-4}$alkyl, $C_{1-4}$alkoxy, $C_{1-4}$alkoxy$C_{1-4}$alkyl, nitro, cyano, trifluoromethyl, trifluoromethoxy, hydroxy, hydroxyalkyl, $C_{1-4}$alkanoyl, $C_{1-4}$alkoxycarbonyl, amino or mono- or dialkylamino;

X is $CH_2$, S or O;

n is zero, 1 or 2;

and salts thereof.

In the compounds of formula (I) an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-pentyl, and the like.

Representative aryl groups or moieties present in any of the substituents $R^2, R^3, R^4$ and $R^5$ in compounds of formula (I) include phenyl, naphthyl, and tetrahydronaphthyl. Suitable examples of heteroaryl groups include both 5 and 6-membered heterocycles containing one or more oxygen, sulphur or nitrogen atoms, such as furyl, thienyl, pyrrolyl, oxazolyl, thiazolyl, imidazolyl, oxadiazolyl, thiadiazolyl, pyridyl, pyridazyl, pyrimidyl and pyrazyl. Suitable substituents for said aryl and heteroaryl groups include halogen, $C_{1-4}$alkyl, $C_{1-4}$alkoxy, $C_{1-4}$alkoxy$C_{1-4}$alkyl, nitro, cyano, trifluoromethyl, trifluoromethoxy, hydroxy, hydroxyalkyl, $C_{1-4}$alkanoyl, $C_{1-4}$alkoxycarbonyl, amino and mono- or -dialkylamino.

When $R^1$ and $R^2$ together form a group $-(CH_2)_mO_p$ wherein p is 1 it will be appreciated that the oxygen atom is attached to the phenyl ring at the $R^2$ position:

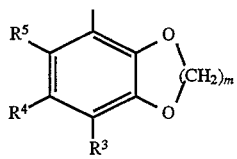

When the $(CH_2)_m$ moiety is substituted by two $C_{1-4}$alkyl groups these are preferably substituted on the same carbon atom e.g. a gem-dimethyl substituent.

In the group —$SO_2NR^{11}R^{12}$, when $NR^{11}R^{12}$ forms a 3- to 8-membered fully saturated heterocyclic ring this may be for example an azetidinyl, pyrrolidinyl, piperidinyl or azacycloheptyl ring. Examples of a 5- to 8-membered partially saturated heterocyclic ring include 1,2,3,6-tetrahydropyridinyl, and examples of a 5- to 8-membered fully saturated heterocyclic ring which contains in addition to the nitrogen atom an oxygen or sulphur atom include morpholinyl or thiomorpholinyl.

In the compounds of Formula (I) $R^1$ preferably represents methyl, ethyl or isopropyl.

Preferably at least one of $R^2$ to $R^5$ is hydrogen, and the other substituents are selected from halogen, $C_{1-2}$alkyl, $C_{1-2}$alkoxy, $C_{1-4}$alkylsulphonyl, phenylsulphonyl, benzylsulphonyl and —$SO_2NR^{11}R^{12}$ wherein $R^{11}$ and $R^{12}$ represent $C_{1-4}$alkyl (e.g. methyl, ethyl, n-propyl or iso-propyl) or $C_{1-2}$alkoxy$C_{1-2}$alkyl (e.g. methoxyethyl), or $NR^{11}R^{12}$ represents a ring selected from azetidinyl, pyrrolidinyl, piperidinyl, azacycloheptyl, 1,2,3,6-tetrahydropyridinyl, 4-morpholinyl or 4-thiomorpholinyl.

In particular one of $R^2$ to $R^5$, e.g. $R^4$, represents $C_{1-4}$alkylsulphonyl, phenylsulphonyl, benzylsulphonyl or a group —$SO_2NR^{11}R^{12}$ and the remaining substituents $R^2$ to $R^5$ are selected from hydrogen, halogen, $C_{1-2}$alkyl and $C_{1-2}$alkoxy. Thus, for example, $R^2$ may be hydrogen, halogen e.g. bromine, methyl or methoxy and $R^3$ and $R^5$ may be hydrogen.

Preferably $R^4$ is $C_{1-4}$alkylsulphonyl, particularly ethylsulphonyl.

Preferably $R^2$, $R^3$ and $R^5$ are all hydrogen.

Preferably $R^6$ is ethyl.

When any of $R^2$ to $R^5$ represent halogen, this may be fluorine, chlorine, bromine or iodine.

It will be appreciated that for use in medicine the salts of formula (I) should be physiologically acceptable. Suitable physiologically acceptable salts will be apparent to those skilled in the art and include for example acid addition salts formed with inorganic acids e.g. hydrochloric, hydrobromic, sulphuric, nitric or phosphoric acid; and organic acids e.g. succinic, maleic, acetic, fumaric, citric, tartaric, acetic, benzoic, p-toluenesulphonic, methanesulphonic or naphthalenesulphonic acid. Other non-physiologically acceptable salts may be used, for example in the isolation of compounds of formula (I) and are included within the-scope of this invention. Also included within the scope of the invention are solvates and hydrates of compounds of formula (I).

When an asymmetric centre is present in a compound of formula (I) the compound will exist in the form of optical isomers (enantiomers). The present invention includes within its scope all such enantiomers and mixtures, including racemic mixtures, thereof. In addition, all possible diastereomeric forms (individual diastereomers and mixtures thereof) of compounds of formula (I) are included within the scope of the invention.

Particular compounds according to the invention include:
2-(5-ethylsulfonyl-2-methoxyphenyl)-5-[N-ethyl-N-1-(1,2,3,4-tetrahydronaphthyl)-aminomethyl]-1H-pyrrole,
2-(5-ethylsulfonyl-2-methoxyphenyl)-5-[N-ethyl-N-1-(indanyl)aminomethyl]-1H-pyrrole,
2-[N-(3,4-dihydro-2H-benzopyran-4-yl)-N-ethylaminomethyl]-5-(5-ethylsulfonyl-2-methoxyphenyl)-1H-pyrrole,
2-[N-(benzocycloheptan-1-yl)-N-ethylaminomethyl]-5-(5-ethylsulfonyl-2-methoxyphenyl)-1H-pyrrole,
2-[N-(3,4-dihydro-2H-benzothiopyran-4-yl)-N-ethylaminomethyl]-5-(5-ethylsulfonyl-2-methoxyphenyl)-1H-pyrrole,
and salts thereof.

Compounds of formula (I) may be prepared by methods analogous to those known in the art, as described hereinafter. Unless stated otherwise, $R^1$–$R^{10}$, n and X are as defined for formula (I).

The present invention also provides a process for preparing compounds of formula (I) which process comprises:

(a) carrying out a Mannich reaction with a compound of formula (II):

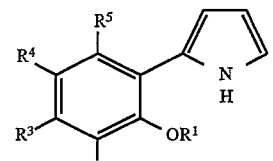

Formula II and an amine of formula (III)

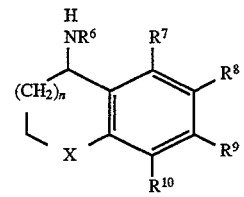

Formula (III)

in the presence of formaldehyde;

(b) carrying out a Vilsmeier reaction with a compound of formula (II) and an amide of formula (IV):

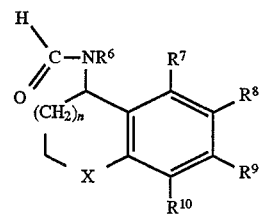

Formula (IV)

followed by reduction of the intermediate product with, for example, sodium borohydride or cyanoborohydride;

(c) reductive amination of a compound of formula (V):

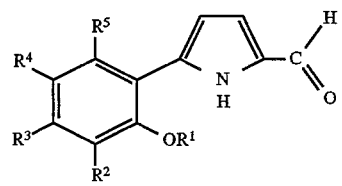

Formula (V)

with an amine of formula (III);
and optionally thereafter forming a salt of formula (I).

The Mannich reaction according to process (a) may be effected according to conventional methods. Thus for example the amine (III) may first be reacted with formaldehyde and the product subsequently reacted with a compound of formula (II). The reaction is preferably effected in a protic solvent, for example an alcohol such as ethanol. An organic or inorganic acid, e.g. acetic acid may be employed as a catalyst.

The Vilsmeier reaction according to process (b) may also be effected according to conventional methods. Thus, for example, the amide of formula (IV) may first be reacted with phosphorus oxychloride and the resulting product subsequently reacted with a compound of formula (II). The product of this reaction is then reduced with, for example, sodium borohydride or cyanoborohydride. These reactions are preferably carried out in a non-protic solvent, for example dichloroethane.

Reductive amination according to process (c) will generally be carried out using a reducing agent such as sodium borohydride or cyanoborohydride and in the presence of a Lewis acid such as titanium (IV) chloride. Reaction of a compound (III) with the amine may conveniently be effected in a solvent such as dichloromethane or dichloroethane.

A compound of formula (II) may be prepared by cyclisation of a dicarbonyl compound of formula (VI):

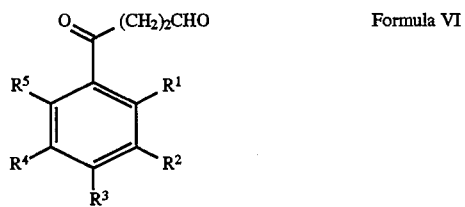

Formula VI

The reaction may be effected using an ammonium salt, e.g. ammonium acetate, in a solvent such as ethanol. (See, for example, C. G. Kruse et al., Heterocycles, vol 26, P3141, 1987).

A compound of formula (VI) may itself be prepared by reacting the appropriate substituted benzoyl halide with a metallo derivative of a 2-(2-haloethyl)-1,3-dioxolane and subsequent acid hydrolysis.

An amine of formula (III) may be prepared by standard methods, for example by reduction of the corresponding amide of formula (VII):

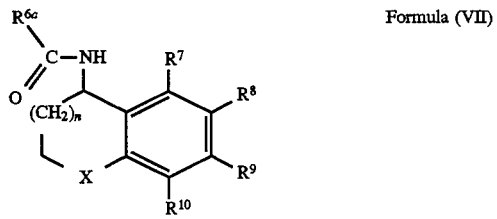

Formula (VII)

wherein $R^{6a}$ is hydrogen, $C_{1-5}$alkyl, $C_{2-5}$alkenyl, $C_{3-6}$cycloalkyl or $C_{3-6}$cycloalkyl$C_{1-3}$alkyl;
with a reducing agent such as lithium aluminium hydride. An amide (VII) may itself be prepared by acylation of the corresponding primary amine with an acylating agent such as an acid chloride.

Alternatively an amine (III) may be obtained by reductive amination of a ketone of formual (VIII):

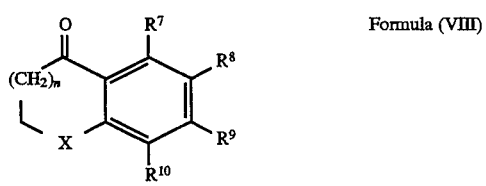

Formula (VIII)

with an amine $R^6NH_2$, in the presence of a titanium (IV) chloride followed by reduction with e.g. sodium cyanoborohydride, as described above for process (c).

An amide of formula (IV) may be prepared by reacting an amine of formula (III) with acetic anhydride in formic acid.

A compound of formula (V) may itself be prepared by carrying out a Vilsmeier reaction in which dimethylformamide is reacted with phosphorous oxychloride and the product reacted with a compound of formula (II), in a solvent such as dichloroethane, followed by acid hydrolysis.

When a component of formula (I) is obtained as a mixture of enantiomers these may be separated by conventional methods such as crystallisation in the presence of a resolving agent, or chromatography, for example using a chiral HPLC column.

Compounds of formula (I) have been found to exhibit affinity for dopamine receptors, in particular $D_3$ receptors, and are expected to be useful in the treatment of disease states which require modulation of such receptors, such as psychotic conditions. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347:146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors. In particular compounds of formula (I) are dopamine $D_3$ receptor antagonists and as such are of potential use as antipsychotic agents for example in the treatment of schizophrenia, schizo-affective disorders, psychotic depression and mania. Other conditions which may be treated by modulation of dopamine $D_3$ receptors include dyskinetic disorders such as Parkinson's disease, neuroleptic-induced parkinsonism and tardive dyskinesias; depression; and drug (eg. cocaine) dependency.

In a further aspect therefore the present invention provides a method of treating conditions which require modulation of the dopamine $D_3$ receptor, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of the dopamine $D_3$ receptor, for example psychoses such as schizophrenia.

For use in medicine, the compounds of the present invention are usually administered as a standard pharmaceutical composition. The present invention therefore provides in a further aspect pharmaceutical compositions comprising a compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The invention is further illustrated by the following non-limiting examples:

DESCRIPTION 1

N-Ethyl-N-1-[1,2,3,4-tetrahydronaphthyl]amine a. A solution of acetyl chloride (1.35 ml, 0.019 mol) in dichloromethane (5 ml) was added dropwise at 0° C. to a solution of 1,2,3,4-tetrahydro-1-naphthylamine hydrochloride (3.16 g, 0.019 mol) and triethylamine (5.4 mol, 0.04 mol) in dichloromethane (50 ml), under argon. The reaction mixture was stirred overnight at room temperature, then dilute hydrochloric acid added dropwise. The layers were separated, and the organic layer dried ($Na_2SO_4$) and evaporated in vacuo to give a solid (2.91 g) which was used in the next stage without further purification.

b. Crude amide (2.84 g, 0.017 mol) was added portionwise to a stirred suspension of lithium aluminium hydride (1.01 g, 0.025 mol) in dry ether (100 ml) under argon. After stirring overnight at room temperature, water (1 ml), sodium hydroxide solution (1 ml, 15%) and water (3 ml) were added dropwise. The mixture was filtered and the filtrate washed with water and dried ($Na_{w}SO_4$). Evaporation of solvent in vacuo gave the title compound as a yellow oil (1.5 g).

$^1$H NMR ($CDCl_3$)δ 1.17 (t, 3H), 1.65–1.80 (m, 1H), 1.80–2.05 (m, 4H, inc. NH), 2.60–2.90 (m, 4H), 3.77 (apparent t, 1H), 7.05–7.20 (m, 3H), 7.33 (m, 1H).

DESCRIPTION 2

1-Ethylaminoindane

Prepared from 1-aminoindane using methods similar to Description 1.

$^1$H NMR ($CDCl_3$)δ: 1.57 (3H, t, J=7 Hz), 1.40 (1H, br s), 1.85 (1H, m), 2.40 (1H, m), 2.77 (3H, m), 3.01 (1H, m), 4.27 (1H, t, J=6.5 Hz), 7.1–7.4 (4H, m)

DESCRIPTION 3

4-Ethylamino-3,4-dihydro-2H-benzopyran

Prepared according to the method of McCarthy et al (*Tetrahedron Letters* 1990, 31, 5547) using 4-chromanone and ethylamine (26% yield).

$^1$H NMR ($CDCl_3$)δ: 1.05–1.20 (1H, br s), 1.15 (3H, t, J=7 Hz), 1.91–2.06 (2H, m) 2.71–2.85 (2H, m), 3.77 (1H, t, J=4 Hz), 4.20–4.24 (1H, m), 4.30–4.35 (1H, m), 6.80–6.90 (2H, m) and 7.12–7.26 (2H, m).

DESCRIPTION 4

1-Ethylamino-benzocycloheptane

Prepared by a method analogous to description 3, but using 1-benzosuberone in place of 4-chromanone. The crude product was purified by chromatography on silica eluting with dichloromethane-methanol (0–3%).

Found M$^+$189.1528; $C_{13}H_{19}N$ requires 189:1517

DESCRIPTION 5

N-Formyl-N-(benzocycloheptan-1-yl)ethylamine

1-Ethylamino-benzocycloheptane (1 g, 5.3 mmol) was treated with formic acid (1.22 ml, 32 mmol) and triethylamine (1 ml, 7.2 mmol) and the mixture was heated under reflux for 22 hours under an argon atmosphere. After cooling to room temperature, the mixture was partitioned between diethyl ether (165 ml) and 5% aqueous NaHCO$_3$ (100 ml). The organic layer was separated, dried (Na$_2$SO$_4$) and evaporated to a brown oil (1.06 g, 93%)

$^1$H NMR (CDCl$_3$)δ: 1.22 (3H, t, J=7 Hz), 1.30–1.50 (1H, m), 1.70–2.26 (5H, m), 2.79–2.90 (2H, m), 3.20–3.38 (1H, m), 3.50–3.67 (1H, m), 4.64 and 5.18 (1H, 2xd), 6.95–7.05 (1H, m), 7.09–7.24 (3H, m), 8.25 and 8.36 (1H, 2xs).

DESCRIPTION 6

4-Ethylamino-3,4-dihydro-2H-benzothiopyran

Prepared by a method analogous to description 3 but using thiochroman-4-one in place of 4-chromanone. The crude product was purified by chromatography on silica eluting with dichloromethane-methanol (0–3%)

Found: M$^+$193.0928; C$_{11}$H$_{15}$NS requires 193.0925

DESCRIPTION 7

N-Formyl-N-[4-(3,4-dihydro-2H-benzothiopyranyl)] ethylamine

This compound was prepared by a method analogous to description 5, but using 4-ethylamino-3,4-dihydro-2H-benzothiopyran in place of 1-ethylamino-benzocychloheptane.

$^1$H NMR (CDCl$_3$)δ: 1.14 and 1.22 (3H, 2xt, J=7 Hz), 2.22–2.48 (2H, m), 2.91–3.10 (2H, m), 3.12–3.28 and 3.55–3.69 (2H, 2xm), 4.65–4.75 and 5.62–5.70 (1H, 2xm), 7.02–7.20 (4H, m), 8.02 and 8.39 (1H, 2xs).

EXAMPLE 1

2-(5-Ethylsulfonyl-2-methoxyphenyl)-5-[N-ethyl-N-1-(1,2,3,4-tetrahydronaphthyl)aminomethyl]-1H-pyrrole hydrochloride N-Ethyl-N-1-[1,2,3,4-tetrahydronaphthyl]amine (0.408 g, 2.33 mmol) was dissolved in ethanol (10 ml) and aqueous formaldehyde (40%; 0.18 ml, 2.3 mmol) added. After stirring for 5 mins, glacial acetic acid (0.19 ml, 2.3 mmol) was added and the solution stirred for 30 mins, then added dropwise to a solution of 2-(5-ethylsulfonyl-2-methoxyphenyl)-1H-pyrrole (0.5 g, 1.89 mmol). The reaction mixture was stirred at room temperature for 3 days then evaporated in vacuo. Chromatography on aluminia (Brockman grade 1) with ethyl acetate as eluent gave the free base of the title compound (0.47 g) as a gum. The gum was dissolved in ethyl acetate and extracted with 0.1N HCl (3×35 ml). The acid extracts were then extracted with dichloromethane (3×50 ml), which were combined, dried (Na$_2$SO$_4$) and evaporated to give the title compound as a solid (0.46 g).

Found M$^+$452.210876; C$_{26}$H$_{32}$N$_2$O$_3$S requires M$^+$452.213365.

EXAMPLE 2

2-(5-Ethylsulfonyl -2-methoxyphenyl)-5-[N-ethyl-N-1-(indanyl)aminomethyl]-1H-pyrrole, hydrochloride Prepared from 1-ethylaminoindane and 2-(5-ethylsulfonyl-2-methoxyphenyl)-1H-pyrrole using methods similar to Example 1.

Found: C, 61.98; H, 6.45; N, 5.79; C$_{25}$H$_{30}$N$_2$O$_3$S.HCl. 0.5H$_2$O requires C, 62,03; H, 6.66; N, 5.79%

EXAMPLE 3

2-[N-(3,4-Dihydro-2H-benzopyran-4-yl)-N-ethylaminomethyl]-5-(5-ethylsulfonyl-2-methoxyphenyl)-1H-pyrrole hydrochloride Prepared by a method analogous to that used to prepare example 1 but using 4-ethylamino-3,4-dihydro-2H-benzopyran in place of N-ethyl-N-1-(1,2,3,4-tetrahydronaphthyl)amine Found: C, 59.60; H, 6.20; N, 5.55; C$_{25}$H$_{30}$N$_2$O$_4$S. HCl. 0.7H$_2$O requires C, 59.62; H, 6.48; N, 5.56%

EXAMPLE 4

2-[N-(benzocycloheptan-1yl)-N-ethylaminomethyl]-5-(5-ethylsulfonyl-2-methoxyphenyl)-1H-pyrrole N-Formyl-N-(benzocycloheptan-1-yl)ethylamine (0.39 g, 1.81 mmol) was treated with phosphorus oxychloride (0.17 ml, 1.81 mmol) at room temperature under argon. After 30 minutes, 1,2-dichloroethane (1.2 ml) was added at 0° C. followed by a solution of 2-(2-methoxy-5-ethylsulfonylphenyl)-1H-pyrrole (0.4 g, 1.51 mmol) in 1,2-dichloroethane (4 ml). The mixture was allowed to warm to room temperature and stirred for 16 h at 25° C. and then for 6 h at 40° C. Sodium borohydride (0.55 g, 14.5 mmol) was then added at 0° C., and the reaction mixture was warmed to room temperature and stirred for 3 h. Water (2.4 ml) and then methanol (2.4 ml) were added dropwise. More water (30 ml) was added and the borane complex was extracted with dichloromethane (3×30 ml). The combined organics were dried (Na$_2$SO$_4$) and evaporated to an oil which was then treated with methanol (4.8 ml) and conc. HCl (2.4 ml) at room temperature for 16 h. The mixture was diluted with water (25 ml) and basified with 40% aqueous NaOH. Extraction into dichloromethane (3×30 ml), followed by drying (Na$_2$SO$_4$) and evaporation of the organic extracts gave an orange oil (0.73 g). The crude material was purified by chromatography on silica eluting with ethyl acetate (20–50%)—hexane, to give the title compound as an orange oil (0.31 g, 44%)

$^1$H NMR (CDCl$_3$)δ: 1.03 (3H, t, J=7 Hz), 1.25 (3H, t, J=7 Hz), 1.60–2.20 (6H, m) 2.65 (3H, m), 3.12 (2H, q, J=7 Hz), 3.52–3.66 (2H, m), 3.72–3.90 (2H, m), 3.96 (3H, s), 6.09 (1H, t, J=2 Hz), 6.63 (1H, t, J=2 Hz), 7.03–7.20 (4H, m), 7.30–7.39 (1H, m) 7.62 (1H, dd, J=8, 2 Hz), 8.10 (1H, d, J=2 Hz),9.82 (1H, br.s).

EXAMPLE 5

2-[N-(3,4-Dihydro-2H-benzothiopyran-4-yl)-N-ethylaminomethyl]-5-(5-ethylsulfonyl-2-methoxyphenyl)-1H-pyrrole Prepared by a method analogous to that used to prepare example 4 but using N-formyl-N-[4-(3,4-dihydro-2H-benzothiopyranyl)]ethylamine in place of N-formyl-N-(benzocycloheptane-1-yl)ethylamine $^1$H NMR (CDCl$_3$)δ: 1.15 (3H, t, J=7 Hz), 1.28 (3H, t, J=7 Hz), 1.85–2.25 (2H, m), 2.40–2.78 (2H, m), 2.85–3.35 (4H, m), 3.62 (1H, d, J=15 Hz), 3.82 (1H, d, J=15 Hz), 3.90–4.05 (1H, m), 4.06 (3H, s), 6.10 (1H, t, J=2 Hz), 6.63 (1H, t, J=2 Hz), 6.98–7.20 (4H, m), 7.65 (1H, dd, J=8, 2 Hz), 7.69–7.80 (1H, m), 8.09 (1H, d, J=2 Hz) and 9.84 (1H, br.s).

BIOLOGICAL TEST METHODS

The ability of the compounds to bind selectively to human D$_3$ dopamine receptors can be demonstrated by measuring their binding to cloned receptors. The inhibition constants (K$_i$) of test compounds for displacement of [$^{125}$I] iodosulpride binding to human D$_2$ and D$_3$ dopamine receptors expressed in CHO cells have been determined. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at −40° C. Crude cell membranes were prepared by homogenisation followed by high-speed centrifugation, and characterisation of cloned receptors achieved by radioligand binding.

Preparation of CHO cell membranes

Cell pellets were gently thawed at room temperature, and resuspended in about 20 volumes of ice-cold 50 mM Tris salts (pH 7.4@37° C.), 20 mM EDTA, 0.2M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4@37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4@37° C.). The final pellet was resuspended in 50 mM Tris salts (pH 7.4@37° C.), and the protein content determined using bovine serum albumin as a standard (Bradford, M. M. (1976) Anal. Biochem. 72, 248–254).

Binding experiments on cloned dopamine receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4@37° C.), 120 mM NaCl, 5 mM KCl, 2 mM CaCl$_2$, 1 mM MgCl$_2$, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4@37° C.), 120 mM NaCl, 5 mM KCl, 2 mM CaCl$_2$, 1 mM MgCl$_2$. The radioactivity on the filters was measured using a Cobra gamma counter (Canberra Packard). Non-specific binding was defined as the radioligand binding remaining after incubation in the presence of 100 μM iodosulpride. For competition curves, 14 concentrations (half-log dilutions) of competing cold drug were used.

Competition curves were analysed simultaneously whenever possible using non-linear least-squares fitting procedures, capable of fitting one, two or three site models. The compounds of Examples 1 and 2 had IC$_{50}$ values of less than 5 nM at the human D$_3$ receptor.

PHARMACEUTICAL FORMULATIONS

The following represent typical pharmaceutical formulations according to the present invention, which may be prepared using standard methods.

| IV Infusion | |
|---|---|
| Compound of formula (I) | 1–40 mg |
| Buffer | to pH ca 7 |
| Sovent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.

Solvent: Typically water but may also include cyclodextrins (1–100 mg) and co-solvents such as propylene glycol, polyethylene glycol and alcohol.

| Tablet | |
|---|---|
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins

Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

We claim:

1. A compound of formula (I):

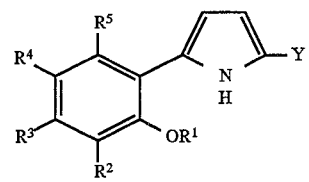

Formula (I)

wherein
R$^1$ represents C$_{1-4}$alkyl; and
R$^2$, R$^3$, R$^4$ and R$^5$ each independently represent hydrogen, halogen, C$_{1-4}$alkyl, C$_{1-4}$alkoxy, C$_{1-4}$alkoxyC$_{1-4}$alkyl, C$_{1-4}$alkylsulphonyl, trifluoromethylsulphonyl; optionally substituted arylsulphonyl, optionally substituted heteroarylsulphonyl, optionally substituted aralkylsulphonyl, optionally substituted heteroaralkylsulphonyl, nitro, cyano, amino, mono- or di-alkylamino, trifluoromethyl, trifluoromethoxy, hydroxy, hydroxyalkyl, C$_{1-4}$alkylthio, C$_{1-4}$alkanoyl, C$_{1-4}$alkoxycarbonyl, C$_{1-4}$alkanoyl, C$_{1-4}$alkoxycarbonyl, C$_{1-4}$alkanoyl, C$_{1-4}$alkoxycarbonyl, or —SO$_2$NR$^{11}$R$^{12}$ wherein R$^{11}$ and R$^{12}$ each independently represent hydrogen, C$_{1-4}$alkyl or C$_{1-4}$alkoxyC$_{1-4}$alkyl, or NR$^{11}$R$^{12}$ forms a 3- to 8- membered fully saturated heterocyclic ring, a 5- to 8-membered partially saturated heterocyclic ring, or a 5- to 8-membered fully saturated heterocyclic ring which contains in addition to the nitrogen atom an oxygen or sulphur atom; or
R$^1$ and R$^2$ together form a linking chain —(CH$_2$)$_m$O$_p$;
wherein m is 2 to 4 and p is zero or 1, which chain may be optionally substituted by one or two C$_{1-4}$alkyl groups; and Y represents a group of formula:

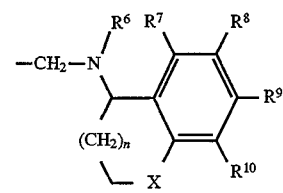

wherein
R$^6$ represents C$_{1-6}$alkyl, C$_{3-6}$-alkenyl or C$_{3-6}$cycloalkylC$_{1-4}$alkyl;

$R^7$, $R^8$, $R^9$ and $R^{10}$ each independently represent hydrogen, hydrogen, $C_{1-4}$alkyl, $C_{1-4}$alkoxy, $C_{1-4}$alkoxy$C_{1-4}$-alkyl, nitro, cyano, trifluoromethyl, trifluoromethoxy, hydroxy, hydroxyalkyl, $C_{1-4}$alkanoyl, $C_{1-4}$alkoxycarbonyl, amino or mono- or dialkylamino;

X is $CH_2$, S or O;

n is zero, 1 or 2;

or a pharmaceutically acceptable salt thereof.

2. A compound according to claim 1 wherein $R^1$ represents methyl, ethyl or isopropyl.

3. A compound according to claim 1 wherein at least one of $R^2$ to $R^5$ is hydrogen, and the other substituents are selected from halogen, $C_{1-2}$alkyl, $C_{1-2}$alkoxy, $C_{1-3}$alkylsulphonyl, phenylsulphonyl, $CF_3$, and $C_{1-2}$dialkylaminosulphonyl.

4. A compound according to claim 1 wherein $R^4$ is $C_{1-4}$alkylsulphonyl and $R^2$, $R^3$ and $R^5$ are all hydrogen.

5. A compound according to claim 1 wherein $R^6$ represents $C_{1-6}$alkyl.

6. A compound according to claim 1 wherein X is $CH_2$.

7. A compound according to claim 1 wherein n is 1.

8. A compound of claim 1 which is 2-(5-ethylsulfonyl-2-methoxyphenyl)-5-[N-ethyl-N-1-(1,2,3,4-tetrahydronaphthyl)aminomethyl]-1H-pyrrole, 2-(5-ethylsulfonyl-2-methoxyphenyl)-5-[N-ethyl-N-1-(indanyl)aminomethyl]-1H-pyrrole, 2-[N-(3,4-dihydro-2H-benzopyran-4-yl)-N-ethylaminomethyl]-5-(5-ethylsulfonyl-2-methoxyphenyl)-1H-pyrrole, 2-[N-(benzocycloheptan-1-yl)-N-ethylaminomethyl]-5-(5-ethylsulfonyl-2-methoxyphenyl)-1H-pyrrole, or 2-[N-(3,4-dihydro-2H-benzothiopyran-4-yl)-N-ethylaminomethyl]-5-(5-ethylsulfonyl-2-methoxyphenyl)-1H-pyrrole, or a pharmaceutically acceptable salt thereof.

9. A process for preparing a compound of claim 1 which process comprises:

(a) carrying out a Mannich reaction with a compound of formula (II):

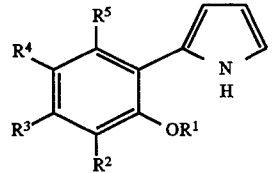

Formula II and an amine of formula (III)

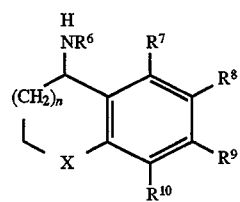

Formula (III)

in the presence of formaldehyde;

(b) carrying out a Vilsmeier reaction with a compound of formula (II) and an amide of formula (IV):

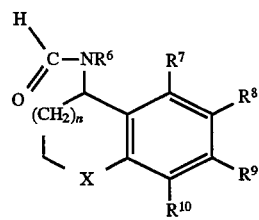

Formula (IV)

followed by reduction of the intermediate product;

(c) reductive amination of a compound of formula (V):

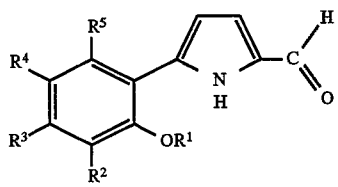

Formula (V)

with an amine of formula (III);

and optionally thereafter forming a salt of formula (I), wherein in formulae (II), (III), (IV) and (V), $R^1$–$R^{12}$, X and n are as defined in claim 1.

10. A method of treating a condition which requires modulation of the dopamine $D_3$ receptor, which comprises administering to a subject in need thereof an effective amount of a compound of claim 1.

11. A pharmaceutical composition comprising a compound of claim 1 and a physiologically acceptable carrier.

* * * * *